(12) United States Patent
Haight et al.

(10) Patent No.: US 8,927,723 B2
(45) Date of Patent: Jan. 6, 2015

(54) PREPARATION OF PYRIDONECARBOXYLIC ACID ANTIBACTERIALS

(71) Applicant: AbbVie, Inc., North Chicago, IL (US)

(72) Inventors: Anthony Haight, Wadsworth, IL (US); David M. Barnes, Lake Villa, IL (US); Geoff G. Z. Zhang, Libertyville, IL (US)

(73) Assignee: AbbVie, Inc., North Chicago, IL (US)

( * ) Notice: Subject to any disclaimer, the term of this patent is extended or adjusted under 35 U.S.C. 154(b) by 0 days.

(21) Appl. No.: 14/176,334

(22) Filed: Feb. 10, 2014

(65) Prior Publication Data

US 2014/0155610 A1 Jun. 5, 2014

Related U.S. Application Data

(63) Continuation of application No. 13/663,601, filed on Oct. 30, 2012, now Pat. No. 8,648,196, which is a continuation of application No. 12/543,240, filed on Aug. 18, 2009, now Pat. No. 8,299,254, which is a continuation of application No. 11/191,319, filed on Jul. 28, 2005, now Pat. No. 7,576,216.

(60) Provisional application No. 60/617,327, filed on Oct. 8, 2004, provisional application No. 60/592,893, filed on Jul. 30, 2004.

(51) Int. Cl.
 *C07D 215/38* (2006.01)
 *C07D 401/14* (2006.01)
 *C07D 205/04* (2006.01)
 *C07D 213/73* (2006.01)
 *C07D 213/75* (2006.01)

(52) U.S. Cl.
 CPC ............ *C07D 401/14* (2013.01); *C07D 205/04* (2013.01); *C07D 213/73* (2013.01); *C07D 213/75* (2013.01)
 USPC ....................................................... 546/156

(58) Field of Classification Search
 USPC ....................................................... 546/156
 See application file for complete search history.

(56) References Cited

U.S. PATENT DOCUMENTS 8,497,378 B2 * 7/2013 Hanselmann et al. ........ 546/159

* cited by examiner

*Primary Examiner* — D M Seaman
(74) *Attorney, Agent, or Firm* — Wilmer Cutler Pickering Hale and Dorr LLP

(57) ABSTRACT

A process for making 1-(6-amino-3,5-difluoropyridin-2-yl)-8-chloro-6-fluoro-7-(3-hydroxyazetidin-1-yl)-4-oxo-1,4-dihydro-3-quinolinecarboxylic acid, and therapeutically acceptable salts thereof, and intermediates used in the process are disclosed.

1 Claim, No Drawings

PREPARATION OF PYRIDONECARBOXYLIC ACID ANTIBACTERIALS

CROSS-REFERENCE TO RELATED APPLICATIONS

This application is a continuation of and claims the benefit of priority of U.S. patent application Ser. No. 13/663,601, filed Oct. 30, 2012, now U.S. Pat. No. application Ser. No. 8,648,196, which is a continuation of and claims the benefit of priority of U.S. patent application Ser. No. 12/543,240, filed Aug. 18, 2009, now U.S. Pat. No. 8,299,254, which is a continuation of and claims the benefit of priority of U.S. patent application Ser. No. 11/191,319, filed Jul. 28, 2005, now U.S. Pat. No. 7,576,216, which claims priority to U.S. Provisional Patent Application No. 60/617,327, filed Oct. 8, 2004 and U.S. Provisional Patent Application No. 60/592,893, filed Jul. 30, 2004, the entire disclosures of which are incorporated by reference herein.

FIELD OF THE INVENTION

This invention pertains to processes for preparing pyridonecarboxylic acid derivatives having antibacterial properties and intermediates which are useful in the process.

BACKGROUND OF THE INVENTION

Many compounds having a pyridonecarboxylic acid moiety re known to be useful as antibacterials. For example, a series of novel quinolone antibacterials appears in PCT Application No. PCT/JP96/02710, published as WO97/11068 on Mar. 27, 1997 and issued in United States as U.S. Pat. No. 5,998,436 on Dec. 7, 1999, U.S. Pat. No. 6,133,284 on Oct. 17, 2000, and U.S. Pat. No. 6,156,903 on Dec. 5, 2000.

There is therefore an existing need for processes for making these compounds in large scale quantities.

SUMMARY OF THE INVENTION

One embodiment of this invention, therefore, pertains to a process for making 2,6-diamino-3,5-difluoropyridine, or a salt thereof, comprising:

(a) reacting 2,3,5,6-tetrafluoropyridine, a compound having formula (I)

or a salt thereof, wherein $R^1$ is phenyl or naphthyl, each of which is unsubstituted or substituted with one or two independently selected —O(CH$_3$) or —O(CH$_2$CH$_3$) substituents, and $R^2$ is hydrogen, —CH$_3$, —CH$_2$CH$_3$, or $R^1$ and a phosphate base at about 50° C. to about 70° C. for a first reaction time and at about 150° C. to about 170° C. for a second reaction time, wherein the total reaction time is about 16 hours to about 24 hours, to provide a compound having formula (II)

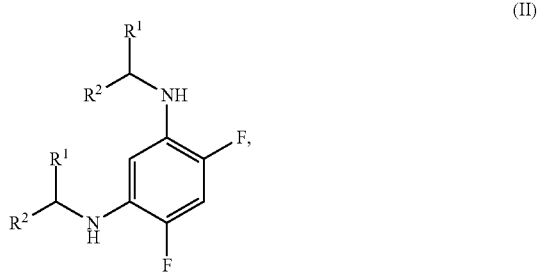

and isolating or not isolating the compound having formula (II);

(b) reacting, for about 45 minutes to about 2 hours, the compound having formula (II), hydrogen and a hydrogenolysis catalyst in water and a co-solvent, wherein the water is present in about 0.1 to about 6 molar equivalents per molar equivalent of the compound having formula (II).

Another embodiment pertains to 2,6-diamino-3,5-difluoropyridine, or a salt thereof, prepared as described in the preceding embodiment.

Still another embodiment pertains to a process for making 2,6-diamino-3,5-difluoropyridine, or a salt thereof, comprising:

(a) reacting 2,3,5,6-tetrafluoropyridine, benzylamine and a phosphate base at about 50° C. to about 70° C. for a first reaction time and at about 150° C. to about 170° C. for a second reaction time, wherein the total reaction time is about 16 hours to about 24 hours, to provide $N^2,N^6$-dibenzyl-2,6-diamino-3,5-difluoropyridine;

(b) reacting, for about 45 minutes to about 2 hours, the $N^2,N^6$-dibenzyl-2,6-diamino-3,5-difluoropyridine, hydrogen and a hydrogenolysis catalyst in water and a co-solvent, wherein the water is present in about 0.1 to about 6 molar equivalents per molar equivalent of the $N^2,N^6$-dibenzyl-2,6-diamino-3,5-difluoropyridine.

Still another embodiment pertains to 2,6-diamino-3,5-difluoropyridine, or a salt thereof, prepared as set forth in the preceding embodiment.

Still another embodiment pertains to a process for making 2,6-diamino-3,5-difluoropyridine, or a salt thereof, comprising:

(a) reacting 2,3,5,6-tetrafluoropyridine, benzylamine and a plurality of potassium phosphate particles having a mean diameter of about 420 micrometers (40 mesh) to about 2000 micrometers (10 mesh) at about 50° C. to about 70° C. for a first reaction time and at about 150° C. to about 170° C. for a second reaction time, wherein the total reaction time is about 16 hours to about 24 hours, to provide $N^2,N^6$-dibenzyl-2,6-diamino-3,5-difluoropyridine;

(b) reacting for about 45 minutes to about 2 hours the $N^2,N^6$-dibenzyl-2,6-diamino-3,5-difluoropyridine, formic acid and 20% palladium on carbon in water and a co-solvent, wherein the water is present in about 0.1 to about 6 molar equivalents per molar equivalent of the $N^2,N^6$-dibenzyl-2,6-diamino-3,5-difluoropyridine.

Still another embodiment pertains to 2,6-diamino-3,5-difluoropyridine, or a salt thereof, prepared as set forth in the preceding embodiment.

Still another embodiment pertains to a process for making 2,6-diamino-3,5-difluoropyridine, or a salt thereof, comprising:

(a) reacting 2,3,5,6-tetrafluoropyridine, benzylamine and a plurality of potassium phosphate particles having a mean diameter of about 420 micrometers (40 mesh) to about 2000 micrometers (10 mesh) at about 50° C. to about 70° C. for about 15 minutes to about 5 hours and at about 150° C. to about 170° C. for about 10 hours to about 20 hours to provide $N^2,N^6$-dibenzyl-2,6-diamino-3,5-difluoropyridine.

(b) reacting, for about 45 minutes to about 2 hours, the $N^2,N^6$-dibenzyl-2,6-diamino-3,5-difluoropyridine, formic acid and 20% palladium on carbon in water and isopropyl acetate, wherein the water is present in about 1 to about 5 molar equivalents per molar equivalent of the $N^2,N^6$-dibenzyl-2,6-diamino-3,5-difluoropyridine.

Still another embodiment pertains to 2,6-diamino-3,5-difluoropyridine, or a salt thereof, prepared as set forth in the preceding embodiment.

Still another embodiment pertains to a process for making a compound having formula (V)

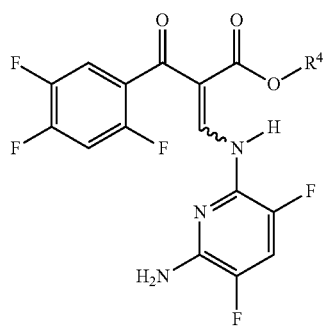

(V)

or a salt thereof, wherein $R^4$ is alkyl, comprising:

(c) reacting, at about 100° C. to about 140° C., a compound having formula (IV)

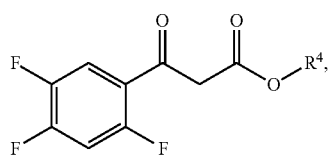

(IV)

and a trialkylorthoformate for about 30 minutes to about 2 hours and reacting the product therefrom and a carboxylic anhydride for about 30 minutes to about 12 hours; and (d) reacting the product of step (c) and 2,6-diamino-3,5-difluoropyridine to provide a product mixture comprising the compound having formula (V), mixing or not mixing the product mixture and water, and isolating or not isolating the compound having formula (V).

Still another embodiment pertains to a compound having formula (V) prepared as set forth in the preceding embodiment.

Still another embodiment pertains to a process for making ethyl (2E/Z)-3-((6-amino-3,5-difluoropyridin-2-yl)amino)-2-(2,4,5-trifluorobenzoyl)-2-propenoate, or a salt thereof, comprising:

(c) reacting, at about 100° C. to about 140° C., ethyl 3-oxo-3-(2,4,5-trifluorophenyl)propanoate and a trialkylorthoformate for about 30 minutes to about 2 hours and reacting the product therefrom and a carboxylic anhydride for about 30 minutes to about 12 hours; and (d) reacting the product of step (c) and 2,6-diamino-3,5-difluoropyridine to provide a product mixture comprising the ethyl (2E/Z)-3-((6-amino-3,5-difluoropyridin-2-yl)amino)-2-(2,4,5-trifluorobenzoyl)-2-propenoate, mixing or not mixing the product mixture and water, and isolating or not isolating the ethyl (2E/Z)-3-((6-amino-3,5-difluoropyridin-2-yl)amino)-2-(2,4,5-trifluorobenzoyl)-2-propenoate.

Still another embodiment pertains to (2E/Z)-3-((6-amino-3,5-difluoropyridin-2-yl)amino)-2-(2,4,5-trifluorobenzoyl)-2-propenoate, or a salt thereof, prepared as set forth in the preceding embodiment.

Still another embodiment pertains to a process for making ethyl (2E/Z)-3-((6-amino-3,5-difluoropyridin-2-yl)amino)-2-(2,4,5-trifluorobenzoyl)-2-propenoate, or a salt thereof, comprising:

(c) reacting, at about 100° C. to about 140° C., ethyl 3-oxo-3-(2,4,5-trifluorophenyl)propanoate and triethylorthoformate for about 30 minutes to about 2 hours and reacting the product therefrom and acetic anhydride for about 30 minutes to about 12 hours; and (d) reacting the product of step (c) and 2,6-diamino-3,5-difluoropyridine to provide a product mixture comprising the ethyl (2E/Z)-3-((6-amino-3,5-difluoropyridin-2-yl)-amino)-2-(2,4,5-trifluorobenzoyl)-2-propenoate, mixing or not mixing the product mixture and water, and isolating or not isolating the ethyl (2E/Z)-3-((6-amino-3,5-difluoropyridin-2-yl)amino)-2-(2,4,5-trifluorobenzoyl)-2-propenoate.

Still another embodiment pertains to (2E/Z)-3-((6-amino-3,5-difluoropyridin-2-yl)amino)-2-(2,4,5-trifluorobenzoyl)-2-propenoate, or a salt thereof, prepared as set forth in the preceding embodiment.

Still another embodiment pertains to a process for making ethyl (2E/Z)-3-((6-amino-3,5-difluoropyridin-2-yl)amino)-2-(2,4,5-trifluorobenzoyl)-2-propenoate, or a salt thereof, comprising:

(c) reacting, at about 110° C. to about 115° C., ethyl 3-oxo-3-(2,4,5-trifluorophenyl)propanoate and triethylorthoformate for about 30 minutes to about 2 hours and reacting the product therefrom and acetic anhydride for about 30 minutes to about 12 hours; and (d) reacting the product of step (c) and 2,6-diamino-3,5-difluoropyridine to provide a product mixture comprising the ethyl (2E/Z)-3-((6-amino-3,5-difluoropyridin-2-yl)amino)-2-(2,4,5-trifluorobenzoyl)-2-propenoate, mixing or not mixing the product mixture and water, and isolating or not isolating the ethyl (2E/Z)-3-((6-amino-3,5-difluoropyridin-2-yl)amino)-2-(2,4,5-trifluorobenzoyl)-2-propenoate.

Still another embodiment pertains to (2E/Z)-3-((6-amino-3,5-difluoropyridin-2-yl)amino)-2-(2,4,5-trifluorobenzoyl)-2-propenoate, or a salt thereof, prepared as set forth in the preceding embodiment.

Still another embodiment pertains to a process for making ethyl (2E/Z)-3-((6-amino-3,5-difluoropyridin-2-yl)amino)-2-(2,4,5-trifluorobenzoyl)-2-propenoate, or a salt thereof, comprising:

(c) reacting, at about 110° C. to about 115° C., ethyl 3-oxo-3-(2,4,5-trifluorophenyl)propanoate and triethylorthoformate for about 30 minutes to about 2 hours and reacting the product therefrom and acetic anhydride for about 30 minutes to about 12 hours; and (d) reacting the product of step (c) and 2,6-diamino-3,5-difluoropyridine to provide a product mixture comprising the ethyl (2E/Z)-3-((6-amino-3,5-difluoropyridin-2-yl)amino)-2-(2,4,5-trifluorobenzoyl)-2-propenoate, mixing the product mixture and water, and isolating the ethyl (2E/Z)-3-((6-amino-3,5-difluoropyridin-2-yl)amino)-2-(2,4,5-trifluorobenzoyl)-2-propenoate.

Still another embodiment pertains to (2E/Z)-3-((6-amino-3,5-difluoropyridin-2-yl)amino)-2-(2,4,5-trifluorobenzoyl)-2-propenoate, or a salt thereof, prepared as set forth in the preceding embodiment.

Still another embodiment pertains to a process for making substantially pure 3-azetidinol hydrochloride comprising:

(e) reacting (±)-2-(chloromethyl)oxirane, sodium bicarbonate and the compound having formula (I) to provide a compound having formula (VI),

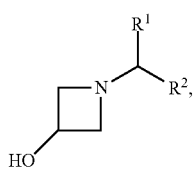

reacting the compound having formula (VI) and either hydrogen chloride at about −10° C. to about 0° C. or (2E/Z)-2-butenedioic (maleic) acid at about 35° C. to about 45° C., and isolating either the hydrochloride salt or the maleate acid salt, respectively, of the compound having formula (VI);

(f) reacting or not reacting the product of step (e) and a base; and (g) reacting the product of step (f), hydrogen and a hydrogenolysis catalyst in a reaction medium consisting essentially of water, an alcohol, and an organic acid, at about 40 psi to about 60 psi and at about 50° C. to about 70° C., for about two hours to about four hours, and isolating the product, with the proviso that when the product of step (e) is the maleate salt, step (f) is conducted.

Still another embodiment pertains to 3-azetidinol hydrochloride prepared as set forth in the preceding embodiment.

Still another embodiment pertains to a process for making substantially pure 3-azetidinol hydrochloride comprising:

(e) reacting (±)-2-(chloromethyl)oxirane, sodium bicarbonate and benzylamine to provide 1-benzyl-3-azetidinol, reacting the 1-benzyl-3-azetidinol and (2E/Z)-2-butenedioic acid at about 35° C. to about 45° C., and isolating 1-benzyl-3-azetidinol (2E/Z)-2-butenedioate;

(f) reacting the product of step (e) and potassium carbonate; and (g) reacting the product of step (f), hydrogen and Pd(OH)₂ on carbon in a reaction medium comprising water, an alcohol and an organic acid at about 40 psi to about 60 psi and about 50° C. to about 70° C. for about two hours to about four hours, reducing the water in the reaction medium to less than about 4 mg per mL and treating the reaction medium first with hydrogen chloride gas between about 0° C. and about 20° C. and then with toluene at about 40° C.

Still another embodiment pertains to 3-azetidinol hydrochloride prepared as set forth in the preceding embodiment.

Still another embodiment pertains to a process for making substantially pure 3-azetidinol hydrochloride comprising:

(e) reacting (±)-2-(chloromethyl)oxirane, sodium bicarbonate and benzylamine in acetonitrile and water to provide 1-benzyl-3-azetidinol, reacting the 1-benzyl-3-azetidinol and (2E/Z)-2-butenedioic acid at about 35° C. to about 45° C., and isolating 1-benzyl-3-azetidinol (2E/Z)-2-butenedioate;

(f) reacting the product of step (e) and potassium carbonate; and (g) reacting the product of step (f), hydrogen and Pd(OH)₂ on carbon in a reaction medium comprising water, isopropanol and acetic acid at about 40 psi to about 60 psi and about 50° C. to about 70° C. for about 2 to about 4 hours, reducing the water in the reaction medium to less than about 4 mg per mL, and treating the reaction medium first with hydrogen chloride gas between about 0° C. and about 20° C. and then with toluene at about 40° C.

Still another embodiment pertains to 3-azetidinol hydrochloride prepared as set forth in the preceding embodiment.

Still another embodiment pertains to a process for making substantially pure 3-azetidinol hydrochloride comprising:

(e) reacting (±)-2-(chloromethyl)oxirane, sodium bicarbonate and benzylamine at about 0° C. to about 80° C. in acetonitrile and water to provide 1-benzyl-3-azetidinol, reacting the 1-benzyl-3-azetidinol and (2E/Z)-2-butenedioic acid at about 40° C., and isolating 1-benzyl-3-azetidinol (2E/Z)-2-butenedioate;

(f) reacting the 1-benzyl-3-azetidinol (2E/Z)-2-butenedioate and potassium carbonate; and (g) reacting the product of step (f), hydrogen and Pd(OH)₂ on carbon in a reaction medium comprising water, isopropanol and acetic acid at about 40 psi and about 65° C. for about two hours, reducing the water in the reaction medium to less than about 4 mg per mL and treating the reaction medium first with hydrogen chloride gas between about 0° C. and about 20° C. and then with toluene at about 40° C.

Still another embodiment pertains to 3-azetidinol hydrochloride, or a salt thereof, prepared as set forth in the preceding embodiment.

Still another embodiment pertains to a process for making a compound having formula (VII)

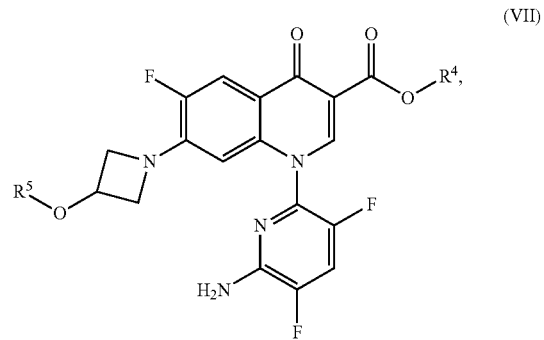

or a salt thereof,
wherein $R^5$ is hydrogen or $C(O)R^6$, wherein $R^6$ is alkyl, phenyl or naphthyl, each of which is unsubstituted or substituted with one or two or three of independently selected $OCH_3$, $OCH_2CH_3$, F, Cl or Br, comprising:

(h) reacting the compound having formula (V) or a salt thereof, a non-protic acid and a bicyclic amine base;

(i) reacting the product of step (h), 3-azetidinol hydrochloride and the bicyclic amine base and isolating or not isolating the product; and (j) reacting or not reacting the product of step (i) and a OH protecting group precursor and isolating or not isolating the product.

Still another embodiment pertains to a compound having formula (VII), or a salt thereof, prepared as set forth in the preceding embodiment.

Still another embodiment pertains to a compound having formula (VII), or a salt thereof, for use in preparing
1-(6-amino-3,5-difluoropyridin-2-yl)-8-chloro-6-fluoro-7-(3-(isobutyryloxy)azetidin-l-yl)-4-oxo-1,4-dihydro-3-quinolinecarboxylic acid,
1-(6-amino-3,5-difluoropyridin-2-yl)-8-chloro-6-fluoro-7-(3-hydroxy-l-azetidinyl)-4-oxo-1,4-dihydro-3-quinolinecarboxylic acid, or a salt, ester or salt of an ester thereof.

Still another embodiment pertains to a compound having formula (VII), or a salt thereof.

Still another embodiment pertains to a compound having formula (VIIa)

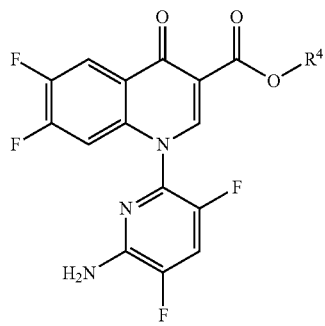

(VIIa)

prepared as set forth in the preceding embodiment.

Still another embodiment pertains to a process for making ethyl 1-(6-amino-3,5-difluoropyridin-2-yl)-6-fluoro-7-(3-(isobutyryloxy)azetidin-l-yl)-4-oxo-1,4-dihydroquinoline-3-carboxylate, or a salt thereof, comprising:
(h) reacting ethyl (2E/Z)-3-((6-amino-3,5-difluoropyridin-2-yl)amino)-2-(2,4,5-trifluorobenzoyl)-2-propenoate, or a salt thereof, a non-protic acid and a bicyclic amine base and not isolating or isolating the product;
(i) reacting the product of step (h), 3-azetidinol hydrochloride and a bicyclic amine base and not isolating the product; and
(j) reacting the product of step (i) and isobutyric anhydride and isolating or not isolating the product.

Still another embodiment pertains to 1-(6-amino-3,5-difluoro-2-pyridinyl)-6,7-difluoro-4-oxo-1,4-dihydro-3-quinolinecarboxylic acid, or a salt thereof prepared as set forth in the preceding embodiment.

Still another embodiment pertains to ethyl 1-(6-amino-3,5-difluoropyridin-2-yl)-6-fluoro-7-(3-(isobutyryloxy)azetidin-1-yl)-4-oxo-1,4-dihydroquinoline-3-carboxylate, or a salt thereof, prepared as set forth in the preceding embodiment.

Still another embodiment pertains to ethyl 1-(6-amino-3,5-difluoropyridin-2-yl)-6-fluoro-7-(3-(isobutyryloxy)azetidin-1-yl)-4-oxo-1,4-dihydroquinoline-3-carboxylate, or a salt thereof, for use in preparing
1-(6-amino-3,5-difluoropyridin-2-yl)-8-chloro-6-fluoro-7-(3-hydroxyazetidin-1-yl)-4-oxo-1,4-dihydro-3-quinolinecarboxylic acid, or a salt, ester or salt of an ester thereof.

Still another embodiment pertains to ethyl 1-(6-amino-3,5-difluoropyridin-2-yl)-6-fluoro-7-(3-(isobutyryloxy)azetidin-1-yl)-4-oxo-1,4-dihydroquinoline-3-carboxylate, or a salt thereof.

Still another embodiment pertains to a process for making ethyl 1-(6-amino-3,5-difluoropyridin-2-yl)-6-fluoro-7-(3-(isobutyryloxy)azetidin-1-yl)-4-oxo-1,4-dihydroquinoline-3-carboxylate, or a salt thereof, comprising:
(h) reacting ethyl (2E/Z)-3-((6-amino-3,5-difluoropyridin-2-yl)amino)-2-(2,4,5-trifluorobenzoyl)-2-propenoate, or a salt thereof, lithium chloride and DBU and not isolating the product;
(i) reacting the product of step (h), 3-azetidinol hydrochloride and DBU and not isolating the product; and
(j) reacting the product of step (i) and isobutyric anhydride and isolating or not isolating the product.

Still another embodiment pertains to ethyl 1-(6-amino-3,5-difluoropyridin-2-yl)-6-fluoro-7-(3-(isobutyryloxy)azetidin-1-yl)-4-oxo-1,4-dihydroquinoline-3-carboxylate, or a salt thereof, prepared as set forth in the preceding embodiment.

Still another embodiment pertains to ethyl 1-(6-amino-3,5-difluoropyridin-2-yl)-6-fluoro-7-(3-(isobutyryloxy)azetidin-1-yl)-4-oxo-1,4-dihydroquinoline-3-carboxylate, or a salt thereof, for use in preparing
1-(6-amino-3,5-difluoropyridin-2-yl)-8-chloro-6-fluoro-7-(3-hydroxyazetidin-1-yl)-4-oxo-1,4-dihydro-3-quinolinecarboxylic acid, or a salt, ester or salt of an ester thereof.

Still another embodiment pertains to a process for making 1-(6-amino-3,5-difluoropyridin-2-yl)-8-chloro-6-fluoro-7-(3-hydroxyazetidin-1-yl)-4-oxo-1,4-dihydro-3-quinolinecarboxylic acid, or a salt thereof, comprising:
(k) reacting the compound having formula (VII), or a salt thereof, and a chlorinating agent and isolating or not isolating a compound having formula (VIII)

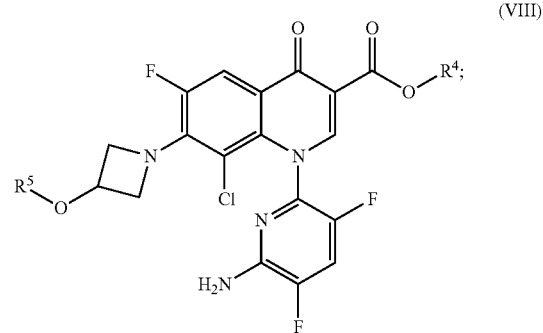

(VIII)

(l) reacting the product of step (k) and a hydroxide base; and
(m) isolating the product of step (l).

Still another embodiment pertains to a compound having formula (VIII), or a salt thereof, prepared as set forth in the preceding embodiment.

Still another embodiment pertains to a compound having formula (VIII), or a salt thereof, for use in the preparation of 1-(6-amino-3,5-difluoropyridin-2-yl)-8-chloro-6-fluoro-7-(3-hydroxyazetidin-1-yl)-4-oxo-1,4-dihydroquinoline-3-carboxylic acid or a salt thereof.

Still another embodiment pertains to a compound having formula (VIII).

Still another embodiment pertains to a process for making 1-(6-amino-3,5-difluoropyridin-2-yl)-8-chloro-6-fluoro-7-(3-hydroxyazetidin-1-yl)-4-oxo-1,4-dihydroquinoline-3-carboxylic acid, or a salt thereof, comprising:
(k) reacting ethyl 1-(6-amino-3,5-difluoropyridin-2-yl)-6-fluoro-7-(3-(isobutyryloxy)azetidin-1-yl)-4-oxo-1,4-dihydroquinoline-3- carboxylate or a salt thereof and N-chlorosuccinimide and isolating or not isolating the product;

(l) reacting the product of step (k) and sodium hydroxide; and (m) isolating the product of step (l).

Still another embodiment pertains to 1-(6-amino-3,5-difluoropyridin-2-yl)-8-chloro-6-fluoro-7-(3-hydroxyazetidin-1-yl)-4-oxo-1,4-dihydro-3-quinolinecarboxylic acid prepared as set forth in the preceding embodiment.

DETAILED DESCRIPTION OF THE INVENTION

This invention pertains to pyridonecarboxylic acid derivatives having antibacterial properties and intermediates which are useful in the process.

Variable moieties are represented by identifiers (capital letters with numerical and/or alphabetical superscripts) and may be specifically embodied.

The term "alkyl," as used herein, means $C_1$-alkyl, $C_2$-alkyl, $C_3$-alkyl, $C_4$-alkyl, $C_5$-alkyl, and $C_6$-alkyl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl, and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl, and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl, and 4-methylpent-2-yl.

The term "alcohol," as used herein, means methanol, ethanol, isopropanol, tert-butanol, and the like or a mixture thereof.

The term "alkanoyl halide," as used herein, means a compound having formula $R^6C(O)Cl$, wherein $R^6$ is alkyl which is unsubstituted or substituted with one or two or three of independently selected $OCH_3$, $OCH_2CH_3$, F, Cl or Br.

The term "aryloyl halide," as used herein, means a compound having formula $R^6C(O)Cl$, wherein $R^6$ is phenyl or naphthyl, each of which is unsubstituted or substituted with one or two or three of independently selected $OCH_3$, $OCH_2CH_3$, F, Cl or Br.

The effect of the solubility of compounds having formula (VII), wherein $R^4$ is ethyl and $R^6$ is variable, in ethyl acetate, is shown in TABLE 1.

| $R^6$ | solubility (mg/mL) |
|---|---|
| $CH_3$ | 1.7 |
| $CH_2CH_3$ | 0.2 |
| $CH(CH_3)_2$ | 6.4 |
| phenyl | 0.2 |

The term "amine base," as used herein, means triethylamine, N-methylmorpholine, and diisopropylethylamine.

The term "base," as used herein, means $Na_2CO_3$, $NaHCO_3$, $K_2CO_3$, $KHCO_3$, triethylamine, diisopropylethylamine and the like, or a mixture thereof.

The term "bicyclic amine base," as used herein, means 1,5-diazabicyclo-[4.3.0]non-5-ene (DBN) and 1,8-diazabicyclo[5.4.0]undec-7-ene (DBN).

The term "carboxylic anhydride," as used herein, means acetic anhydride, butyric anhydride, isobutyric anhydride and the like.

The term "chlorinating agent," as used herein, means N-chlorosuccinimide, thionyl chloride, $Cl_2$, $Cl_2O$ and the like with or without water and with or without an acid such as sulfuric acid, phosphoric acid, trifluoroacetic acid, perchloric acid and the like.

The yields of chlorinations of compounds having formula (VII), wherein $R^4$ is $CH_2CH_3$ and $R^5$ is $C(O)R^6$, wherein $R^6$ is $CH(CH_3)_2$, with N-chlorosuccinimide in ethyl acetate is shown in TABLE 2.

| acid/additive | amount (equivalents) | yield (%) |
|---|---|---|
| TFA/water | 0.1-0.2 | 83 |
| $HClO_4$ | 0.1-0.2 | 95 |
| $H_3PO_4$ | 0.1 | 90 |
| $H_2SO_4$ | 0.065 | 90 |

The term "hydrogenolysis catalyst," as used herein, means water-wet or not water-wet 5% palladium hydroxide, water-wet or not water-wet 10% palladium hydroxide, water-wet or not water-wet 5% palladium hydroxide on carbon, water-wet or not water-wet 10% palladium hydroxide on carbon, and the like or mixtures thereof.

The term "hydroxide base," as used herein, means the hydroxide base of sodium, potassium, lithium, barium and the like or mixtures thereof.

The term "non-protic acid," as used herein, means lithium chloride, magnesium chloride, zinc chloride and the like, or mixtures thereof.

The term "OH protecting group precursor," as used herein, means a carboxylic anhydride, an alkanoyl halide, an aryloyl chloride and the like.

The term "organic acid," as used herein, means formic acid, acetic acid, propionic acid and the like, or mixtures thereof.

The term "phosphate base," as used herein, means $K_3PO_4$, $K_2HPO_4$, $KH_2PO_4$, $Na_3PO_4$, $Na_2HPO_4$, $NaH_2PO_4$, and the like or mixtures thereof The term "substantially pure 3-azetidinol hydrochloride," as used herein, means 3-azetidinol hydrochloride having a low enough solvent content to be in powder form.

The term "trialkylorthoformate" means trimethylorthoformate, triethylorthoformate, triisopropylorthoformate and the like, or mixtures thereof.

Compounds of this invention can have one or more than one asymmetrically substituted carbon atoms in the R or S configuration. Compounds having asymmetrically substituted carbon atoms enriched with one configuration over the other are assigned the configuration which is present in the higher amount, preferably 85% to 95% enrichment, more preferably 95% to 99% enrichment, and still more preferably greater than 99% enrichment. Accordingly, compounds of this invention can exist as enantiomers, mixtures of enantiomers, diastereomers having relative stereochemistry, diastereomers having absolute stereochemistry, diastereomers having at least one asymmetrically substituted carbon atom which is enriched in one configuration and at least one asymmetrically substituted carbon atom which is not enriched, and mixtures of the preceding.

Compounds of this invention can also have one or more than one carbon-carbon double bond or carbon-nitrogen double bond. Accordingly, compounds of this invention can exist as geometric isomers of either Z or E configuration or as mixtures of geometric isomers.

The terms "R", "S", "Z", and "E" are as defined by the IUPAC 1974 Recommendations for Section E, Fundamental Stereochemistry, Pure Appl. Chem. (1976) 45, 13-10.

Compounds of this invention may exist as acid addition salts or base addition salts and may be prepared during their isolation or following their purification. Acid addition salts of compounds are prepared by reaction with acid. For example, the acetate, adipate, alginate, bicarbonate, citrate, aspartate, benzoate, benzenesulfonate, bisulfate, butyrate, camphorate, camphorsufonate, citrate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate, and undecanoate salts of compounds of this invention are meant to be embraced thereby. Base addition salts of compounds of this invention may be prepared by reaction with a base such as the hydroxide, carbonate, bicarbonate, phosphate, hydrogen phosphate, or dihydrogen phosphate of cations such as calcium, iron, lithium, potassium, sodium or magnesium.

The following examples are meant to further embody the compounds and processes of this invention.

EXAMPLE 1

A solution of benzylamine (73 Kg) in water (650.4 Kg) at 0° C. was treated with epichlorohydrin (61 Kg), stirred for approximately 2 hours until solid formed, stored at 10° C. for 16 hours, and filtered. The filtrant was mixed with sodium bicarbonate (104 Kg) in acetonitrile (1110 Kg), and the mixture was azeotropically distilled with acetonitrile addition to maintain a volume of 900 L, diluted with acetonitrile (400 L), stirred at 75° C. for 10-16 hours, cooled to ambient temperature, filtered through diatomaceous earth (Celite®), concentrated to 300 L, added over 1 hour to a solution of maleic acid (52.8 Kg) in acetonitrile (310 Kg) at 40° C., cooled to 0° C., and filtered. The filtrant was washed with isopropyl acetate and dried to provide 113.6 Kg of product. Mp 127-129° C.; $^1$H NMR (CD$_3$OD) δ 7.54-7.51 (m, 5H), 6.33 (s, 2H), 4.98 (brs, 4H, exchangeable), 4.72 (quintet, J=6 Hz, 1H), 4.45 (s, 2H), 4.39 (m, 2H), 4.01 (m, 2H), 3.38 (CHD$_2$OD).

EXAMPLE 2

A suspension of EXAMPLE 1 (111.6 Kg) in ethyl acetate (605 Kg) was treated with 25% aqueous potassium carbonate (560 Kg) until the suspension homogenized. The orgainc layer was isolated and concentrated with an isopropanol azeotrope. The concentrate was mixed with acetic acid (25.8 Kg), added to half-wet 5% palladium hydroxide on carbon (13.1 Kg), stirred at 55-65° C. under hydrogen at 40 psi for 2-8 hours, cooled to ambient temperature, filtered, washed with isopropanol, concentrated with an isopropanol azeotrope to 110 L, cooled to 5-10° C., treated with HCl gas (14 Kg), stirred at ambient temperature for 1 hour and at 40° C. for 30 minutes, treated with toluene (210 Kg) over 1 hour, stirred for 30 minutes, cooled to ambient temperature, and filtered. The filtrant was washed with toluene and dried under vacuum at 50° C. to provide 36.7 Kg of product. $^1$H NMR (CD$_3$OD) δ 4.57 (m, 1H), 4.08 (m, 2H), 3.80 (m, 2H), 3.38 (CHD$_2$OD).

EXAMPLE 3

A suspension of benzylamine (106 Kg) and milled (20 mesh) potassium phosphate (45 Kg) in N-methylpyrrolidinone (100 Kg) at 50° C. was treated with 2,3,5,6-tetrafluoropyridine (30 Kg), stirred for 30 minutes at 50-70° C. and at 165° C. for 12-18 hours, cooled to 10° C., treated sequentially with water (240 L) and 50% (v/v) isopropyl acetate/heptane (240 L), isopropyl acetate (37.9 Kg), and water (88.5 Kg), each at 10° C. The bottom and middle layers were separated and washed with 2M HCl (120 L) and water (120 L), each precooled to 10° C., and concentrated. The concentrate was treated with isopropyl acetate (275 Kg) and stored in an opaque container under nitrogen. $^1$H NMR (CDCl$_3$, 300 MHz) δ 7.29-7.24 (m, 10H), 6.97 (t, 1H), 4.57 (s, 4H).

EXAMPLE 4

A mixture of half-wet 20% palladium hydroxide on carbon (68.1 Kg) was treated sequentially with 39.1% (w/w) EXAMPLE 3 in isopropyl acetate (410 Kg total, 160 Kg EXAMPLE 3), isopropyl acetate (550 Kg) and 88% formic acid (57 Kg). The mixture was stirred at 50° C. for 2 hours and filtered under nitrogen through diatomaceous earth (Celite®) with isopropyl acetate (200 Kg) rinsing. The filtrate was washed twice with 6% citric acid solution having its pH adjusted to 4 with potassium hydroxide (water (200 Kg)/citric acid (12 Kg)/potassium hydroxide (2 Kg)), 1M sodium bicarbonate solution (150 Kg) and water (150 Kg) and concentrated. The concentrate was treated with heptane(1005 Kg) over 90 minutes, and the solution was cooled to 0° C. and filtered. The filtrant was washed with heptane (220 Kg) and dried under vacuum at 40° C. to provide 61.5 Kg of product, which was stored in an opaque container under nitrogen. $^1$H NMR (CDCl$_3$, 300 MHz) δ 7.03 (t, 1H), 4.5-4.0 (brs, 4H).

EXAMPLE 5

A solution of 2,4,5-trifluorobenzoic acid (139.5 Kg) in DMF (8.4 Kg) and toluene (613 Kg) was treated with thionyl chloride (139.4 Kg), stirred at 60° C. for 3.5 hours, cooled to 25° C., concentrated to 20% of its original volume, treated with toluene (600 Kg), distilled and stored at ambient temperature.

EXAMPLE 6

A suspension of potassium ethyl malonate (50.8 Kg) and magnesium chloride (34.5 Kg) in toluene (130 Kg) below 0° C. was treated with THF (265 L), cooled to 0° C., treated with triethylamine (75 Kg), warmed to 50° C., stirred for 1-5 hours, cooled to 0° C., treated with 22% (w/w) of EXAMPLE 5 in toluene (163 Kg), warmed to ambient temperature, stirred for 2 hours, added to 2M HCl (407 Kg), stirred for 30 minutes, separated from the water layer and washed with water. This procedure was repeated, and the organic layers were combined, concentrated with an ethanol (150 L) azeotrope, treated with water (30% by weight of the organic layer), stirred for 3 hours at 0° C., and filtered. The filtrant was washed with 3:1 ethanol/water and dried under vacuum at 35-45° C. to provide 86 Kg of product. $^1$H NMR (CDCl$_3$) (keto) δ 7.75 (ddd, J=10.8, 10.8, 6.0 Hz, 1H), 7.02 (ddd, 1H), 4.27 (q, J=7.2 Hz, 2H), 3.95 (d, 4.2 Hz, 2H), 1.35 (t, J=7.3 Hz, 3H); (enol) δ 12.72 (s, 1H), 7.85 (ddd, J=10.5, 9.6, 6.6 Hz, 1H), 6.96 (ddd, J=10.5, 10.5, 6.6 Hz, 1H), 5.84 (s, 1H), 4.23 (q, J=7.2 Hz, 2H), 1.27 (t, J=7.4 Hz, 3H).

EXAMPLE 7A

A solution of EXAMPLE 6 (83.2 Kg) in triethyl orthoformate (80.1 Kg) at reflux was stirred for 0.5-1 hour, treated with acetic anhydride (103.5 Kg), stirred for 12 hours and cooled to ambient temperature to provide a solution that was used immediately.

EXAMPLE 7B

The solution of EXAMPLE 7A was treated with N-methylpyrrolidinone (210 Kg), acetonitrile (161 Kg) and water (3 Kg), added to a suspension of EXAMPLE 4 (57.4 Kg) in 1:1 N-methylpyrrolidinone (210 Kg) and acetonitrile (161 Kg), stirred for 2 hours, added to water (662 Kg) and filtered. The filtrant was washed with (2:1) acetonitrile/water and water and dried under vacuum at 60° C. to provide 119.5 Kg of product. Mp 157-160° C.; $^1$H NMR (CDCl$_3$, 300 MHz) (E) δ 1.15 (t, 3H), 4.16 (q, 2H), 4.64 (br s, 2H), 6.90 (m, 1H), 7.22 (t, 1H), 7.32 (m, 1H), 9.03 (d, 1H), 12.44 (bd, 1H); (Z) δ 1.03 (t, 3H), 4.11 (q, 2H), 4.60 (br s, 2H), 6.90 (m, 1H), 7.20 (t, 1H), 7.48 (m, 1H), 8.90 (d, 1H), 11.17 (bd, 1H).

EXAMPLE 8A

A mixture of EXAMPLE 7 (115 Kg) and lithium chloride (24.3 Kg) in N-methylpyrrolidinone (769 Kg) below 35° C. was treated with DBU (946.1 Kg) and stirred for 2 hours to provide a solution of EXAMPLE 8A that was used immediately.

EXAMPLE 8B

The solution of EXAMPLE 8A below 40° C. was treated with EXAMPLE 2 (33.9 Kg) and DBU (109 Kg) and stirred for 2-5 hours to provide a solution of EXAMPLE 8B that was used immediately.

EXAMPLE 8C

The solution of EXAMPLE 8B was treated with isobutyric anhydride (99.7 Kg), stirred at 35° C. for 1-2 hours, cooled to 20-30° C., treated with ethyl acetate (104 Kg) and 10% aqueous citric acid (570 Kg) and filtered. The filtrant was washed with water and dried under vacuum at 50° C. to provide 136 Kg of product. $^1$H NMR (DMSO-d$_6$, 400 MHz) δ 8.49 (s, 1H), 8.00 (dd, J=9.0, 9.3 Hz, 1H), 7.75 (d, J=12.8 Hz, 1H), 6.79 (br s, 2H), 5.95 (dd, J=1.5, 7.6 Hz, 1H), 5.21 (m, 1H), 4.36 (t, J=7.4 Hz, 2H), 4.02 (q, J=7.0 Hz, 2H), 3.95 (dd, J=3.7, 9.2 Hz, 2H), 2.58 (hept, J=7.0 Hz, 1H), 1.26 (t, J=7.0 Hz, 3H), 1.11 (d, J=7.0 Hz, 6H).

EXAMPLE 9A

A suspension of EXAMPLE 8C (99.8 Kg) in dichloromethane (813 Kg) at 0-5° C. was treated with 1,3-dichloro-5,5-dimethylhydantoin (39.5 Kg) in dichloromethane (540 Kg) over 2 hours then with 10% aqueous sodium bisulfite (550 Kg), separated from the water layer, washed with 5% sodium bicarbonate and water and concentrated. The concentrate was dissolved in methyl tert-butyl ether, crystallized at 5° C. and dried at 65° C. to provide 109 Kg of product as the methyl tert-butyl ether solvate. $^1$H NMR (CDCl$_3$) methyl tert-butyl ether solvate: δ 8.35 (s, 1H), 7.95 (d, J=14.7 Hz, 1H), 7.24 (t, J=8.9 Hz, 1H), 5.19-5.11 (m, 1H), 4.82-4.72 (m, 2H), 4.39-4.27 (m, 2H), 4.35 (q, J=7.5 Hz, 2H), 3.19 (s, 3H), 2.57 (sept, J=7.1 Hz, 1H), 1.36 (t, J=7.4 Hz, 3H), 1.17 (d, J=7.1 Hz, 6H), 1.18 (s, 9H).

EXAMPLE 9B

A suspension of EXAMPLE 8C (110 Kg) and N-chlorosuccinimide (31 Kg) in ethyl acetate (785 Kg) at 0-5° C. was treated with phosphoric acid (2.5 Kg) and water (1 Kg) while the temperature was kept at less than 5° C., warmed to 22° C., stirred for 3 hours, washed with sodium bicarbonate solution and 10% sodium sulfite solution and concentrated. The concentrate was treated with methyl tert-butyl ether (403 Kg), and the slurry was stirred at 35° C. for 30 minutes, cooled to 5° C. and filtered.

EXAMPLE 9C

A suspension of EXAMPLE 8C (4.91 g) and N-chlorosuccinimide (1.36 g) in ethyl acetate (500 mL) was treated with trifluoroacetic acid (0.15 mL) over 3 hours then with 5% aqueous sodium bicarbonate (25 mL), separated from the water layer, washed with 10% aqueous sodium hydrogen sulfate (10 mL) and concentrated to 50 mL with a methyl tert-butyl ether (250 mL) azeotrope. The concentrate was dissolved in methyl tert-butyl ether, and the solution was stirred at 45° C. until solid formed, cooled to ambient temperature, and filtered. The filtrant was washed with methyl tert-butyl ether and dried under vacuum at 50° C. to provide 5.33 g of product as the methyl tert-butyl ether solvate. $^1$H NMR (CDCl$_3$) δ 8.35 (s, 1H), 7.95 (d, J=14.7 Hz, 1H), 7.24 (t, J=8.9 Hz, 1H), 5.19-5.11 (m, 1H), 4.82-4.72 (m, 2H), 4.39-4.27 (m, 2H), 4.35 (q, J=7.5 Hz, 2H), 3.19 (s, 3H), 2.57 (sept, J=7.1 Hz, 1H), 1.36 (t, J=7.4 Hz, 3H), 1.17 (d, J=7.1 Hz, 6H), 1.18 (s, 9H).

EXAMPLE 10

A solution of N-chlorosuccinimide (25.3 Kg) in methyl acetate (419 Kg) at 17° C. was treated with sulfuric acid (560 g), transferred to a slurry of EXAMPLE 8C (92.7 Kg) in ethyl acetate (244 Kg) at 17° C. while maintaining the reaction temperature at 17° C., quenched/washed with 1.5% aqueous sodium bicarbonate (370 Kg), washed with 10% aqueous sodium sulfite (200 Kg) and concentrated. The concentrate was dissolved in isopropanol, treated with 4% (w/w) aqueous potassium hydroxide (750 Kg), stirred at 50° C. until hydrolysis was complete, passed through a polishing filter, treated with 12% aqueous acetic acid (410 Kg) and filtered. The filtrant was washed with water and dried at 50° C. to provide 73 Kg of product. $^1$H NMR (CDCl$_3$) δ 14.63 (brs, 1H), 8.70 (d, J=0.7 Hz, 1H), 7.95 (dd, J=9.9, 0.7 Hz, 1H), 7.83 (d, J=13.6 Hz, 1H), 6.75 (s, 2H), 5.75 (d, J=5.8 Hz, 1H), 4.61 (m, 12H), 4.47 (m, 1H), 4.18 (m, 2H).

EXAMPLE 11A

A solution of EXAMPLE 6 (3.65 Kg) and triethyl orthoformate (4.93 L) in toluene (18.5 L) at reflux was stirred for 1 hour, treated with acetic anhydride (3.50 L), stirred for 12-24 hours, cooled to ambient temperature and concentrated with a toluene (8 L) azeotrope until no triethyl orthoformate was detected by $^1$H NMR (CDCl$_3$).

EXAMPLE 11B

A solution of EXAMPLE 4 (2.58 Kg) in DMSO (6.75 Kg) at 14° C. was treated with EXAMPLE 11A in DMSO (9.50

Kg) over 1 hour, stirred for 15 minutes, treated with potassium carbonate (2.25 Kg), stirred at 60-70° C. for 1-2 hours, cooled to 30° C., treated sequentially with acetonitrile (13.3 Kg) and 9% aqueous citric acid (20.2 Kg), each over 15 minutes, cooled to ambient temperature and filtered. The filtrant was washed with 9% aqueous citric acid (10 Kg)/acetonitrile (9.1 L) and acetonitrile (2×9.1 L) and dried at 40-45° C. to provide 4.49 Kg of product. $^1$H NMR (DMSO-d6) δ 8.72 (s, 1H), 8.14 (dd, J=11.4, 9.6 Hz, 1H), 8.03 (dd, J=11.2, 9.8 Hz, 1H), 7.51 (ddd, J=12.6, 6.6, 1.2 Hz, 1H), 6.82 (br s, 2H), 4.23 (q, J=7.5 Hz, 2H), 1.28 (t, J=7.5 Hz, 3H).

EXAMPLE 12

A mixture of EXAMPLE 2 (1.46 Kg) and potassium bicarbonate (4.66 Kg) in N-methylpyrrolidinone (36.8 Kg) was stirred at 60° C. for 1 hour, treated with EXAMPLE 11B (4 Kg), stirred for 3 hours, cooled to ambient temperature, treated with N,N-dimethylaminopyridine (65 g) and acetic anhydride (5.34 Kg) while keeping the temperature below 45° C., stirred until the intermediate alcohol was consumed, cooled to ambient temperature, and filtered. The filtrant was washed with N-methylpyrrolidinone (4.3 Kg), and the filtrate was warmed to 70° C., treated with water (40.4 Kg), cooled to ambient temperature, and filtered. The filtrant was washed with water (2×12 Kg) and dried under vacuum at 50° C. to provide 4.36 Kg of product. $^1$H NMR (DMSO-d$_6$) δ 8.31 (d, J=0.7 Hz, 1H), 7.81 (dd, J=8.8, 9.9 Hz, 1H), 7.55 (d, J=12.9 Hz, 1H), 6.62 (br s, 2H), 5.75 (dd, J=1.5, 7.3 Hz, 1H), 5.00 (m, 1H), 4.16 (m, 2H), 4.02 (q, J=7.1 Hz, 2H), 3.77 (dd, J=3.3, 9.6 Hz, 2H), 1.87 (s, 3H), 1.07 (t, J=7.1 Hz, 3H).

EXAMPLE 13

A mixture of EXAMPLE 12 (1.97 Kg) in dichloromethane (15.4 Kg) at 0° C. was treated with 1,3-dimethyl-5,5-dichlorohydantoin (890 g) in dichloromethane (7.7 Kg) over 2.5 hours, stirred for 2 hours, treated with 10% aqueous sodium hydrogen sulfite (10.2 Kg), separated from the water layer, washed with water, filtered, and concentrated with an ethyl acetate (4.2 Kg) azeotrope. The concentrate was treated with ethyl acetate (9 Kg) and heptane (3.5 Kg), stirred at 5° C. for 2 hours, and filtered. The filtrant was washed with 1:1 ethyl acetate/heptane (1.4 Kg) and dried under vacuum to provide 1.84 Kg of product. Mp 193-195° C.; $^1$H NMR (DMSO-d$_6$, 300 MHz) δ 8.42 (d, J=0.7 Hz, 1H), 7.93 (dd, J=9.9, 1.1 Hz, 1H), 7.75 (d, J=13.9 Hz, 1H), 6.72 (br s, 1H), 5.11 (m, 1H), 4.73 (m, 2H), 4.32 (m, 2H), 4.22 (dd, J=14.0, 7.0 Hz, 2H), 2.07 (s, 3H), 1.26 (t, J=14.0 Hz, 3H).

The preceding is meant to be illustrative of this invention and not limiting. Obvious variations and changes are meant to be within the scope of this invention, as defined in the claims.

We claim:
1. A process for making ethyl 1-(6-amino-3,5-difluoropyridin-2-yl)-6-fluoro-7-((3-isobutyryloxy)azetidin-1-yl)-4-oxo-1,4-di hydroquinoline-3-carboxylate, or a salt thereof, comprising:
   (a) reacting ethyl (2E/Z)-3-((6-amino-3,5-difluoropyridin-2-yl)amino)-2-(2,4,5-trifluorobenzoyl) -2-propenoate, or a salt thereof, lithium chloride and 1,8-diazabicyclo [5.4.0]undec-7-ene and not isolating the product;
   (b) reacting the product of step (a), 3-azetidinol hydrochloride and 1,8-diazabicyclo[5.4.0]undec-7-ene and not isolating the product; and
   (c) reacting the product of step (b) and isobutyric anhydride and isolating or not isolating the product.

* * * * *